(12) United States Patent
Rubinfeld

(10) Patent No.: US 6,583,125 B2
(45) Date of Patent: *Jun. 24, 2003

(54) FORMULATION OF NITROGEN MUSTARD

(75) Inventor: Joseph Rubinfeld, Danville, CA (US)

(73) Assignee: SuperGen, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/938,473

(22) Filed: Aug. 23, 2001

(65) Prior Publication Data

US 2002/0058634 A1 May 16, 2002

Related U.S. Application Data

(63) Continuation of application No. 09/684,375, filed on Oct. 5, 2000, now Pat. No. 6,284,747, which is a continuation of application No. 09/347,096, filed on Jul. 2, 1999, now Pat. No. 6,218,374, which is a continuation of application No. 09/143,412, filed on Aug. 28, 1998, now Pat. No. 6,048,845, which is a continuation of application No. 08/790,223, filed on Feb. 3, 1997, now Pat. No. 5,804,568, which is a continuation of application No. 08/297,249, filed on Aug. 26, 1994, now Pat. No. 5,602,112, which is a continuation-in-part of application No. 08/116,724, filed on Sep. 3, 1993, now abandoned, which is a continuation-in-part of application No. 07/911,664, filed on Jun. 19, 1992, now abandoned.

(51) Int. Cl.$^7$ ................ A61K 31/715; A61K 31/04
(52) U.S. Cl. .............................. 514/58; 514/610
(58) Field of Search ................... 514/58, 610

(56) References Cited

U.S. PATENT DOCUMENTS

| | | | |
|---|---|---|---|
| 4,024,223 A | 5/1977 | Noda et al. ............. 424/180 |
| 4,228,160 A | 10/1980 | Szejtli et al. ............. 424/180 |
| 4,232,009 A | 11/1980 | Hayashi et al. ........... 424/180 |
| 4,351,846 A | 9/1982 | Matsumoto et al. ....... 424/305 |
| 4,352,793 A | 10/1982 | Yamahira et al. ......... 424/180 |
| 4,383,992 A | 5/1983 | Lipari .................... 424/238 |
| 4,407,795 A | 10/1983 | Nicolau et al. ........... 424/180 |
| 4,424,209 A | 1/1984 | Tuttle .................... 424/180 |
| 4,425,336 A | 1/1984 | Tuttle .................... 424/180 |
| 4,438,106 A | 3/1984 | Wagu et al. .............. 424/180 |
| 4,474,811 A | 10/1984 | Masuda et al. ........... 424/317 |
| 4,478,995 A | 10/1984 | Shinoda et al. ........... 536/46 |
| 4,479,944 A | 10/1984 | Hayashi et al. ........... 424/180 |
| 4,479,966 A | 10/1984 | Hayashi et al. ........... 424/305 |
| 4,497,803 A | 2/1985 | Harada et al. ............ 514/450 |
| 4,499,085 A | 2/1985 | Masuda .................. 514/58 |
| 4,524,068 A | 6/1985 | Szejtli et al. ............. 514/58 |
| 4,555,504 A | 11/1985 | Jones .................... 514/26 |
| 4,565,807 A | 1/1986 | Uekama et al. ........... 514/58 |
| 4,575,548 A | 3/1986 | Ueda et al. .............. 536/46 |
| 4,596,795 A | 6/1986 | Pitha .................... 514/58 |
| 4,598,070 A | 7/1986 | Ohwaki et al. ........... 514/58 |
| 4,603,123 A | 7/1986 | Chiesi et al. ............. 514/58 |
| 4,608,366 A | 8/1986 | Hasegawa et al. ........ 514/58 |
| 4,623,641 A | 11/1986 | Szejtli et al. ............. 514/58 |
| 4,659,696 A | 4/1987 | Hirai et al. .............. 514/15 |
| 4,663,316 A | 5/1987 | Ninger et al. ............ 514/99 |
| 4,675,395 A | 6/1987 | Fukazawa et al. ......... 536/103 |
| 4,727,064 A | 2/1988 | Pitha .................... 514/58 |
| 4,728,509 A | 3/1988 | Shimizu et al. ........... 424/81 |
| 4,728,510 A | 3/1988 | Shibanai et al. .......... 424/94.5 |
| 4,751,095 A | 6/1988 | Karl et al. ............... 426/548 |
| 4,983,586 A | 1/1991 | Bodor ................... 514/58 |
| 5,024,998 A | 6/1991 | Bodor ................... 514/58 |
| 5,602,112 A * | 2/1997 | Rubinfeld ............... 514/58 |
| 5,804,568 A * | 9/1998 | Rubinfeld ............... 514/58 |
| 6,048,845 A * | 4/2000 | Rubinfeld ............... 514/58 |
| 6,218,374 B1 * | 4/2001 | Rubinfeld ............... 514/58 |
| 6,284,747 B1 * | 9/2001 | Rubinfeld ............... 514/58 |

OTHER PUBLICATIONS

Loftsson et al., "Solubilization and Stabilization of Drugs Through Cyclodextrin Complexation", *Acta Pharm Nord* 3(4), 215–217 (1991).

Windholz et al., *The Merck Index*, 10th Ed., p. 818. Abstract No. 5569 (Mannitol) (1983).

Loftsson et al., "Solubilization and Stabilization of Drugs Through Cyclodextrin Complexation", *Chemical Abstracts* 116 (16), 158718p (1992).

\* cited by examiner

*Primary Examiner*—Kevin E. Weddington
(74) *Attorney, Agent, or Firm*—Shirley Chen Wilson Sonsini Goodrich & Rosati

(57) ABSTRACT

Compositions of matter comprising a substituted cyclodextrin and cytotoxic compound, especially cytotoxic drugs such as antibiotic, anti-fungal and anti-neoplastic, drugs are claimed. The compositions cause significantly less ulceration compared to the same formulation of cytotoxic compound without cyclodextrin compound when extravasated. The compositions may also cause less vascular irritation compared to the same formulation of cytotoxic compound without cyclodextrin when administered intravenously without extravasation. Compositions of matter comprising watersoluble cytotoxic agents, especially anticancer drugs and anti-ulceration effective or anti-irritatioin effective amounts of cyclodextrin compounds are also claimed. Methods for reducing the likelihood of ulceration and or irritation when administering the compositions according to the invention are also disclosed and claimed.

14 Claims, No Drawings

FORMULATION OF NITROGEN MUSTARD

This application is a continuation of U.S. patent application Ser. No. 09/684,375, filed Oct. 5, 2000, now U.S. Pat. No. 6,284,747, which is a continuation of U.S. patent application Ser. No. 09/347,096, filed Jul. 2, 1999, now U.S. Pat. No. 6,218,374, which is a continuation of U.S. patent application Ser. No. 09/143,412, filed Aug. 28, 1998, now U.S. Pat. No. 6,048,845, which is a continuation of U.S. patent application Ser. No. 08/790,223, filed Feb. 3, 1997, now U.S. Pat. No. 5,804,568, which is a continuation of U.S. patent application Ser. No. 08/297,249, filed Aug. 26, 1994, now U.S. Pat. No. 5,602,112, which is a continuation-in-part of U.S. patent application Ser. No. 08/116,724, filed Sep. 3, 1993, now abandoned, which is a continuation-in-part of U.S. patent application Ser. No. 07/900,664 filed Jun. 19, 1992, now abandoned.

FIELD OF THE INVENTION

The present invention relates to improved pharmaceutical formulations.

BACKGROUND OF THE INVENTION

Many compounds that can be injected intravascularly into animal and human patients for a beneficial effect have the undesirable hazardous side effect of causing ulceration at the injection site as a result of extravasation. Extravasation is strictly defined as the forcing of fluid out of a blood or lymph vessel into the surrounding or perivascular tissue. More broadly defined, extravasation may be said to occur when an injection solution and blood or serum combined with an injection solution leaks out of a blood vessel during intravascular administration of the solution or subsequent thereto, at the site of injection, or when the injection solution is accidentally injected into tissue surrounding a blood vessel. Such extravasation may occur as a result of accidentally failing to properly insert a needle for the intravascular administration of a solution into the lumen of a blood vessel. It may also occur by accidentally inserting a needle entirely through a blood vessel intended for intravascular administration. In addition, leakage of solution from a blood vessel may occur if a blood vessel is too small for the rate and volume of injection solution being injected into the blood vessel. Lastly, leakage of solution from a blood vessel may occur if the blood vessel has been damaged or eroded by prior injection or other trauma.

Extravasation of certain intravasuclarly administered compounds may lead to formation of a deep, spreading and painful ulcer which may require surgical extirpation of the affected tissue. Skin grafting is frequently required to repair and reconstruct the resulting wound. Another complication of such intravascularly administered compounds is that they are irritants causing irritation of the lining of the blood vessel into which they are injected. This irritation may be accompanied by pain at the site of injection or along the length of the blood vessel. In addition the irritation may lead to reduced patency of the blood vessel and in some cases may induce the formation of blood clots in the affected blood vessel leading to a risk of gangrene or emboli.

Not all injection solutions cause ulceration as a result of extravasation; however; many pharmaceutical compounds injected for particular chemotherapeutic effects in many therapeutic categories have this presently unavoidable side effect. Pharmaceutical compounds having this side effect are well known to those skilled in the art of administration of such compounds to patients and animal subjects. The side effects of such drugs are collected in a number of publication including the Physicians Desk Reference published yearly by Medical Economics Data, a division of Medical Economics Company Inc., Montvale N.J. 07645 USA and the United States Pharmacopeia Drug Information published and supplemented by the Untied States Pharmacopeial Convention, Inc 12601 Twinbrook Parkway, Rockville, Md. 20852, USA. Similar volumes are published else where in various countries of the world.

Among the pharmaceutical compounds that cause extravasation associated ulceration are cytotoxic compounds which are administered to patients and animal subjects for the purpose of manifesting a specific cytotoxic effect. Such cytotoxic compounds include many anticancer or antineoplastic compounds. These compounds may be synthetic chemical compounds, such as nitrogen mustard derivatives such as mechlorethamine, plant alkaloids such as vincristine and vinblastine, alkylating agents such as dacarbazine and streptozocin or microbially produced and purified or partially purified antibiotics. Cytotoxic antibiotics include those administered as anti-cancer agents, such as mitomycin, bleomycin, daunorubicin, doxorubicin, plicamycin and dactinomycin. In addition antifungal antibiotic agents such as amphoteracin B can cause ulceration associated with extravasation. Furthermore, therapeutic compounds which are not administered to achieve a specific cytotoxic effect may also result in extravasation associated ulceration. For example certain sedative compounds when injected intravasculary (IV) can cause severe ulceration if extravasation occurs. Such sedative compounds include but are not limited to benzodiazapine compounds including diazepam. Thus, there is a long felt need For safer formulations of injectable pharmaceutical compounds to reduce or eliminate ulceration resulting from extravasation.

Pharmaceutical preparations containing cyclodextrin are known. Human sex hormones including, estradiol-, progesterone- and testosterone-hydrophilic cyclodextrin derivatives, especially hydroxypropyl cyclodextrin suitable for oral mucosal or rectal mucosal Administration are disclosed in U.S. Pat. No. 4,596,795. These preparations are disclosed as increasing the circulating half life of the hormone through elimination of absorbance via the gastrointestinal tract and consequent removal by hepatic clearance. There is no disclosure of complexes that reduce local ulceration or irritation at an injection site.

U.S. Pat. No. 4,727,064 disclosed pharmaceutical preparations consisting generally of a drug with a substantially low water solubility and an amorphous water soluble cyclodexrin-based mixture having improved dissolution properties and absorption by the body. The solutions of amorphous water soluble cyclodextrin are disclosed as non-irritating topically, and having low toxicity, both systemic and local, when applied parenterally. None of the amorphous cyclodextrin-drug mixtures disclose in the specification or claims discloses a complex including a drug that causes ulceration when extravasted and there is no disclosure concerning reduction of ulceration as a result of administering the drug in a complex with an amorphous cyclodextrin complex.

A variety of improvements in the characteristics of pharmaceutical complexes including various cyclodextrins and cyclodextrin derivatives are disclosed in the following United States patents, but none of them disclose the reduction in extravasation-associated ulceration, or irritation through the formation of complexes of cyclodextrin and pharmaceutical compounds: Noda et al., U.S. Pat. No. 4,024,223 methyl salicylate; Szejtli et al U.S. Pat. No.

4,228,160 indomethacin; Hyashi et al., U.S. Pat. No. 4,232,009 ω-halo-PGI$_2$ analogs; Matsumoto et al., U.S. Pat. No. 4,351,846 3-hydroxy and 3-oxo prostaglandin analogs; Yamahira et al., U.S. Pat. No. 4,353,793, bencyclane fumarate; Lipari, U.S. Pat. No. 4,383,992 steroids-corticosteroids, androgens anabolic steroids, estrogens, progestagens; Nicolau, U.S. Pat. No. 4,407,795 P-hexadecyla-ninobenzoic acid sodium salt; Tuttle, U.S. Pat. No. 4,424,209 3,4-diisobutyryloxy-N-{3-(4-isobuttyryloxyphenyl)-1-methyl-n-propyl]-β-phenethylamine; Tuttle, U.S. Pat. No. 4,425,336, 3,4-dihydroxy-N-[3-(4-hydroxyphenyl)-1-methyl-n-propyl]-β-phenethylamine; Wagu et al., U.S. Pat. No. 4,438,106 fatty acids EPA and DHA; Masuda et al., U.S. Pat. No. 4,474,881 2-(2-fluoro-4-biphenyl)propionic acid or salt; Shinoda et al., U.S. Pat. No. 4,478,995 acid addition salt of (2'-benzyloxycarbonyl)phenyl trans-4-guanidinomehtylcyclohexanecaboxylate; Hyashi et al., U.S. Pat. No. 4,479,944 Prostaglandin I$_2$ analog; Hayashi et al., U.S. Pat. No. 4,479,966, 6,9-methano-prostaglandin I$_2$ analogs; Harada et al., U.S. Pat. No. 4,497,803 lankacidin-group antibiotic; Masuda U.S. Pat. No. 4,499,085 prostoglandin analog; Szejtli et al., U.S. Pat. No. 4,524,068 piperonyl butoxide; Jones, U.S. Pat. No. 4,555,504 cardiac glycoside; Uekama et al., U.S. Pat. No. 4,565,807 pirprofen; Ueda et al., U.S. Pat. No. 4,575,548 2-nitroxymethyl-6-chloropyridine; Ohwaki et al., U.S. Pat. No. 4,598,070 tripamide anti-hypertensive; Chiesi et al., U.S. Pat. No. 4,603,123 piroxicam (feldene); Hasegawa et al., U.S. Pat. No. 4,608,366 monobenzoxamine; Hiari et al., U.S. Pat. No. 4,659,696 polypeptide; Szejtili et al., U.S. Pat. No. 4,623,641 Prostoglandin I$_2$ methyl ester; Ninger et al., U.S. Pat. No. 4,663,316. unsaturated phosphorous containing antibiotics including phosphotrienin; Fukazawa et al., U.S. Pat. No. 4,675,395 hinokitol; Shimizu et al., U.S. Pat. No. 4,728,509 3-amino-7-isopropyl-5-oxo-5H-[1]-benzopyrano[2,3-b]pyridine-3-carboxcylic acid; Shibani et al., U.S. Pat. No. 4,728,510 milk component Karl et al U.S. Pat. No. 4,751,095 aspartame.

Among the above-mentioned patents, several indicate that complexes of cyclodextrin with drug substances improve side effects of the drug substance. Szejtli et al., U.S. Pat. No. 4,228,160 disclosed that the frequency and severity of gastric and duodenal erosion and ulceration in rats caused by indomethecin is improved in an oral formulation of a complex of β-cyclodextrin: indomethacin in a 2:1 ratio, but is not improved and in fact worsens in the same oral formulation of a complex of β-cyclodextrin: indomethacin in a 1:1 ratio.

Shirmazu et al., U.S. Pat. No. 4,352,793 discloses that a formulation wherein bencyclane fumarate an anti-convulsive compound and β-cyclodextrin or γ-cyclodextrin yield a complex in which the bencyclane fumarate is an inclusion compound. These complexes, when formulated as a liquid suitable for oral administration were claimed to be less irritating in an isotonic buffered pH 7 solution when administered as drops to the eyes of rabbits, as compared to bencyclane fumarate drops at the same drug concentration. Shimazu et al., also discloses that similar complexes dissolved in rabbit blood in vitro yielded reduced hemolysis as compared to equal concentrations of bencyclane fumarate alone mixed with rabbit blood. There was no indication that this compound is cytotoxic or causes ulceration or irritation of the surrounding tissue when extravasated during or after injection.

Masuda et al., U.S. Pat. No. 4,478,811 disclose ophthalmic formulations of β- or γ-cyclodextrin complexes of the nonsteroidal anti-inflammatory compound fluoro-bi-phenylacetic acid which are less irritating and painful than the same formulations of fluoro-bi-phenyl acetic acid alone. There was no indication that this compound is cytotoxic or causes ulceration of the surrounding tissue when extravasated during for after injection.

Shinoda et al., U.S. Pat. No. 4,478,995 disclose complexes of α-, β- and γ-cyclodextrin and acid addition salts of (2-benzyloxycarbonyl)phenyl trans-4-guanidinomehtylcyclo-hexanecaboxylate, and enzyme inhibitor having anti-gastric and duodenal ulcer activity. The complexes were administered orally and were more active in preventing ulceration than oral administration of acid addition salts of (2'-benzyloxycarbonyl)phenyl trans-4-guanidinomehtylcyclo-hexanecaboxylate alone in solution. No preparation suitable for intravenous injection were disclosed and there was no indication that this compound is cytotoxicor causes ulceration of the surrounding tissue when extravasated during for after injection.

Uekama et al., U.S. Pat. No. 4,565,807 discloses complexes of α-, β- and γ-cyclodextrin, pirprofen and a pharmaceutically acceptable base. Piprofen is an analgesic and anti-inflammatory compound which is bitter and can cause irritation to the gastrointestinal tract. The complexes disclosed in the patent have improved less bitter taste and are less gastrointestinal irritating than the un-complexed compound piprofen. No preparation suitable for intravenous injection were disclosed and there was no indication that this compound is cytotoxic or causes ulceration of the surrounding tissue when extravasated during for after injection.

Bekers, O., et al.,"Stabilization of mitomycins on complexation with cyclodextrins in aqueous acidic media" International Journal of Pharmaceutics, 53 (1989) 239–248 describes the investigation of stabilization of mytomycin-C and several related mitomycins by formation of a complex with cyclodextrin. The authors indicate that at the pH ranges studied α- and β-cyclodextrin as sell as heptakis-(2,6,-di-O-methyl)-β-cyclodextrin and (dimethyl-β-cyclodextrin have no influence on stabilization of mitomycin-C pH degradation. γ-cyclodextrin is reported as having measurable stabilizing effect on mitomycin in acidic media at pH above 1. There is no suggestion that stabilization of mitomycin-C from acidic degradation in aqueous media by complexation with γ-cyclodextrin is or can be related to amelioration of ulceration or irritation caused by mitomycin when administered to a patient.

Bodor U.S. Pat. No. 5,024,998 and Bodor U.S. Pat. No. 4,983,586 disclose a series of compositions comprising complexes of :Beta hydroxypropylcyclodextrin (HPCD)-complexed to a difficult to solubilize drug, or HPCD complexed to a drug—which has first been complexed to a specific class of drug carriers characterized as redox drug carriers. The complex of drug and redox carrier is itself difficult to solubilize and is highly lipophilic due to the presence of pyridine derivatives as part of the redox carrier complex. Bodor '998 and '586 further claim that a solution of 20 to 50% hydroxypropylcyclodextrin-and lipophilic drug-redox carrier complex or 20 to 50% hydroxypropylcyclodextrin-and lipophilic and or water labile drug is useful in a method of "decreasing the incidence of precipitation of a lipophilic and/or water labile drug occurring at or near the injection site and/or in the lungs or other organs following parenteral administration.

Neither of the Bodor references mentions the problem of irritation associated with the administration of these water soluble compounds or ulceration associated with their extravasation. Furthermore, neither of the Bodor references teaches or suggests that water soluble cytotoxic or antineoplastic drugs or the water-soluble salts of such drugs when administered with cyclodextrin compounds can significantly decrease ulceration or irritation associated with administration or extravasation of such drugs.

Significantly the Bodor references attribute the precipitation and organ deposition problems associated with parenteral administration of lipophilic drugs to the effects of organic solvents used to solubilized the drug in the parenteral vehicle. The Bodor references additionally state that drugs which are particularly useful in the parenteral composition and methods disclosed therein are those which are relatively insoluble in water but whose water solubility can be substantially improved by formulation with 20 to 50% of the selected cyclodextrin, e.g. HPCD, in water.

Thus it is quite clear that the Bodor references are directed to prevention of the phenomenon of precipitation of insoluble drugs and insoluble drug-carrier complexes. There is no disclosure concerning the prevention of ulceration or irritation or of amounts of the amorphous cyclodextrin useful for the prevention of these two side effects.

SUMMARY AND OBJECTS OF THE INVENTION

The present invention provides a composition of matter comprising an anti-ulceration-effective amount or an anti-irritation-effective amount of an amorphous complex of cyclodextrin and any compound which can cause extravasation-associated ulceration or irritation when injected. In general such compounds are cytotoxic compounds, but the compositions of matter according to the invention are not limited to cytotoxic compounds. For example certain sedative compounds when injected intravascularly (IV) can cause severe ulceration if extravasation occurs. Such sedative compounds include but are not limited to diazepam compounds including diazepam. In addition certain ionotrophic drugs such as dopamine, may lead to ulceration if extravasated or to vascular irritation when injected.

The present invention is useful in the prevention of extravasation-associated ulceration and irritation associated with injection of drugs that are insoluble in water as well as drugs that are soluble in water. It is particularly and unexpectedly effective in prevention of these side effects in the administration of water soluble cytotoxic agents. In particular, the present invention is a composition of matter that marks an improvement in the formulation of cytotoxic agents which are water soluble whereby the tendency of these agents to cause irritation or ulceration when extravasated on injection is substantially eliminated. By combining such water soluble cytotoxic agents with a cyclodextrin compound and preferably an amorphous cyclodextrin such as an alkyl-substituted or hydroxyalkyl-substituted α-, β-, or γ-cyclodextrin compound, irritation or ulceration when extravasated is substantially eliminated. Applicant has further discovered that surprisingly the inclusion of an excipient such as mannitol, sorbitol or lactose further improves the performance of the composition in that the reduction in ulceration is even more pronounced than when the drug is used with the cyclodextrin compound alone.

The phenomena of ulceration and irritation should be understood to be a different side effect than the phenomenon of precipitation which is addressed in the Bodor references. The distinction is clearest in the case of cytotoxic agents and particularly in the case of water soluble cytotoxic agents. In general the lipophilic drugs and drug-carrier complexes that Bodor discloses precipitate at the injection site or near to the side of injection, even when they are properly injected intravenously and not extravasated. Thus the fundamental teaching of the Bodor references relates to solubilization of insoluble drugs so that they do not precipitate from the blood stream of a patient into the blood vessels near the site of injection or in more remote capillary beds of distant organs such as the lung.

By contrast the phenomenon of extravasation occurs when the drug either leaks from a blood vessel into the perivascular tissue or is inadvertently injected into the perivascular tissue. When certain drugs are extravasated they cause ulceration. It will therefor be appreciated that extravasation is particularly threatening when the drug is a water-soluble cytotoxic compound. Such water soluble drugs, instead of precipitating and leading to a localized ulceration, tend to disseminate into more distant tissues from the perivascular tissue immediate to the site of injection. This dissemination leads to extensive ulceration and not localized precipitation. Thus for example there are many reported cases in which localized extravasation of the water soluble agent doxorubicin leads to disseminated ulceration of the whole limb of the patient.

Compositions of matter according to the invention comprising an amorphous complex of cyclodextrin and a cytotoxic compound may comprise a variety of different cytotoxic compounds used for a variety of therapeutic purposes. Such compositions according to the invention include an amorphous complex of cyclodextrin and an anti-cancer, anti-neoplastic, anti-fungal antibiotic, anti-bacterial antibiotic or chemical compound. Especially preferred in the compositions according to the invention are those in which the cytotoxic compound is one that is soluble in aqueous solution. Compounds that are soluble in aqueous solution include those in which the active drug is soluble. Also included are those drugs in which the acid complex of the active compound is soluble in water, such as doxorubicin hydrochloride. Additionally, a salt of an active drug formed to render the drug soluble is included in compounds that are soluble in aqueous. solution. Examples of the latter include vincristine sulfate and vinblastine sulfate (the sulfate salts of the active drug) and erythromycin lactobionate (prepared from erythromycin base and lactobiono-δ-lactone).

The cytotoxic compound may be a synthetic chemical compound such a nitrogen mustard derivative such as mechlorethamine. The cytotoxic compound may be a plant alkaloid such as vincristine and vinblastine or an alkylating agent such as dacarbazine and streptozocin. The compound may be microbially produced and subsequently purified or partially purified antibiotic. Cytotoxic antibiotics that may be part of the composition according to the invention include those administered as anti-cancer agents, such as the mitomycins including but not limited to mitomycin-c, the bleomycins including but not limited to mixtures predominating in bleomycin A2 and B, daunorubicin, doxorubicin, idarubicin plicamycin and dactinomycin. With respect to the compositions of matter comprising an amorphous complex of cyclodextrin and a cytoxic compound which is a chemotherapeutic anticancer agent, the anticancer agent may be a vessicant or an irritant. Composititons of matter in which the anti-cancer agent is a protein biological response modifier such as interleukin-2 or Tumor necrosis factor are not intended as the anti-cancer agents of the composition according to the invention; however compositions of matter which include such protein biologicaal response modifiers and an anti-neoplastic chemotherapeutic agent are intended as compositions according to the invention.

Other cytotoxic antibiotics that may be part of the composition according to the invention include antifungal antibiotic agents such as amphoteracin B and certain antibacterial antibiotics, such as tetracycline and erythromycin that may lead to ulceration if extravasated or to vascular irritation when injected. Additionally, the compositions according to the invention include pharmaceutical compounds which are not administered to achieve a specific cytotoxic effect, but which may also result in extravasation-associated ulceration. Such compounds which may be part of the compositions according to the invention include, for example certain sedative compounds typified by benzodiazapine compounds including but not limited to diazepam.

The compositions of matter according to the invention may also include, in addition to the amorphous complex of cyclodextrin and cytotoxic compound, carriers, bulking agents and other pharmaceutically acceptable excipients such as mannitol, sorbitol, lactose, dextrox and the like. Surprisingly, it has been found that certain chemotherapeutic compounds and such excipients, particularly mannitol, when formulated with cyclodextrin do not cause any significant extravasation when administered to mammalian subjects.

The composition of matter according to the invention may be supplied as a dry powder or as a solution. If the composition of matter is to be injected into a subject it will be rendered sterile prior to injection. Accordingly, the composition of matter according to the invention may be supplied as a sterile cake, plug or powder or as a sterile lyophilized preparation in a sterile vial suitable for the addition of a sterile diluent, or as a sterile liquid solution in a sterile container.

It is an object of the present invention to provide compositions of matter which substantially reduce ulcerationassociated with extravasation caused by compounds which can cause such ulceration comprising an amorphous complex of cyclodextrin and such compound.

Another object of the present invention to provide compositions of matter which substantially reduce ulceration associated with extravasation caused by compounds that are soluble in aqueous solution which can cause such ulceration comprising an amorphous complex of cyclodextrin and such compound that is soluble in aqueous solution.

It is a further object of the present invention to provide compositions of matter which substantially reduce ulceration associated with extravasation caused by cytotoxic drugs which can cause such ulceration comprising an amorphous complex of cyclodextrin and a cytotoxic drug.

It is another object to the invention to provide compositions of matter which substantially reduce ulceration associated with extravasation caused by antibiotics which can cause such ulceration comprising an amorphous complex of cyclodextrin and such an antibiotic.

It is yet another object to the invention to provide compositions of matter which substantially reduce ulceration associated with extravasation caused by antineoplastic drugs which can cause such ulceration comprising an amorphous complex of cyclodextrin and such antineoplastic drugs.

It is an object of the present invention to provide compositions of matter which substantially reduce ulceration associated with extravasation caused by compounds which can cause such ulceration comprising an ulceration reducing amount of an amorphous complex of cyclodextrin and such compound.

Another object of the present invention to provide compositions of matter which substantially reduce ulceration associated with extravasation caused by compounds that are soluble in aqueous solution which can cause such ulceration comprising an ulceration-reducing amount of anamorphous complex of cyclodextrin and such compound that is soluble in aqueous solution.

It is a further object of the present invention to provide compositions of matter which substantially reduce ulceration associated with extravasation caused by cytotoxic drugs which can cause such ulceration comprising an ulceration-reducing amount of an amorphous complex of cyclodextrin and a cytotoxic drug.

It is another object to the invention to provide compositions of matter which substantially reduce ulceration associated with extravasation caused by antibiotics which can cause such ulceration comprising an ulceration-reducing amount of an amorphous complex of cyclodextrin and such an antibiotic.

It is yet another object to the invention to provide compositions of matter which substantially reduce ulceration associated with extravasation caused by antineoplastic drugs which can cause such ulceration comprising an ulceration-reducing amount of an amorphous complex of cyclodextrin and such an antineoplastic agent.

Still another object of the invention is to provide a method for reducing the likelihood of ulceration in subjects in need of parenteral treatment with compounds that if extravasated have the potential for causing ulceration, comprising administering to such subjects a preparation comprising at least one compound that if extravasated has the potential for causing ulceration and an anti-ulceration-effective amount of cyclodextrin or amorphous cyclodextrin.

Yet still another object of the invention is to provide a method for reducing the likelihood of irritation in subjects in need of parenteral treatment with compounds that when administered parenterally, particularly intravenously, have the potential for causing irritation, comprising administering to such subject a preparation comprising at least one compound that has the potential for causing irritation and an anti-irritation-effective amount of cyclodextrin or amorphous cyclodextrin.

DETAILED DESCRIPTION OF THE INVENTION

By cyclodextrin is meant α-, β-, or γ-cyclodextrin. Cyclodextrins are described in detail in Pitha et al., U.S. Pat. No. 4,727,064 which is incorporated herein by reference. Cyclodextrins are cyclic oligomers of glucose; these compounds form inclusion complexes with any drug whose molecule can fit into the lipophile-seeking cavities of the cyclodextrin molecule.

By amorphous cyclodextrin is meant non-crystalline mixtures of cyclodextrins wherein the mixture is prepared from α-, β-, or γ-cyclodextrin. In general the amorphous cyclodextrin is prepared by non-selective additions, especially alkylation of the desired cyclodextrin species. Reactions are carried out to yield mixtures containing a plurality of components thereby preventing crystallization of the cyclodextrin, various alkylated and hydroxyalkyl-cyclodextrins can be made and of course will vary, depending upon the starting species of cyclodextrin and the addition agent used. Among the amorphous cyclodextrins suitable for compositions according to the invention are hydroxypropyl, hydroxyethyl, glucosyl, maltosyl and maltotrosyl derivatives of β-cyclodextrin, carboxyamidomethyl-β-cyclodextrin, carboxymethyl-β-cyclodextrin, hydroxypropyl-β-cyclodextrin and diethylamino-β-cyclodextrin. In the compositions according to the invention hydroxy-β-cyclodextrin is preferred. The substituted γ-cyclodextrins may also be uirable, including hydroxyproply, hydroxyethyl, glucosyl, maltosyl and maltotriosyl derivatives of γ-cyclodextrin.

By cyclodextrin compound is meant cyclodextrin and amorhpous cyclodextrin.

The term "pharmaceutically accepted or acceptable excipient" means an ingredient used in a pharmaceutical preparation which does function as an active agent. Such pharmaceutically acceptable excipients are used for various purposes, such as stabilizers, buffers, suspending agents, carriers and the like and are listed and described in a number of texts including for example, the British Pharmacopeia, the Japanese Pharmacopeia and the United States Pharmacopeia XXII and National Formulary XVII and supplements thereto. Suitable excipients for injectable pharmaceutical compositions are typified by non-reducing sugars or sugar alcohols such as mannitol and sorbitol. Glucose, and lactose may also be used as excipients.

By dactinomycin (actinomycin-D) is meant an antibiotic substance belonging to the actinomycin complex produce by several Streptomyces species having the elemental composition of $C_{62}H_{86}N_{12}O_{16}$, and molecular weight 1255.47. It is sold under the trade name Cosmegen (Merck, Sharp & Dohme) as a sterile lyophilized powder including dactinomycin and mannitol.

By mithramycin is meant an antibiotic substance identified as aurelic acid, produce by several Streptomyces species including *Streptomyces argillaceus* and *Streptomyces tanashiensis*, having the elemental composition of $C_{52}H_{72}O_{24}$, chemical formula [2S-{2 ,3β(1R*.3R*.4S*)}]-6-{(2,6-Dideoxy-3-O-(2,6-dideoxy-β-D-arabino-hexopyranosyl-β-D-arabino-hexopyranosyl]oxy]-2-[O-2,6-dideoxy-3-C-methyl-β-D-ribo-hexopyranosyl-(1-4)-O-2,6-dideoxy- -D-lyxo-hexopyranosyl-(1-3)-2,6-dideoxy-β-D-arabino-hexopyranosyl)oxy]-3-(3,4dihydrox-1-methyl-2oxopentyl)-3,4-dihydro-8,9-dihydroxy-7-methyl-1(2H)-anthracenone molecular weight 1085.18. It is also know under the generic name plicamycin. It is sold under the trade name Mithracin (Miles, Inc. Pharmaceutical Division) as a sterile freeze dried preparation for intravenous administration including mithramycin and mannitol and sufficient disodium phosphate to adjust to pH 7.

By mitomycin-C is meant one of a group of anti-neoplastic antibiotics substances mitomycin-A, -B, and -C produced by *Streptomyces caespitosus* (*griseovanaceseus*). Mitomycin-D has also been isolated from *Streptomyces verticillatus*. Mitomycin-C has the elemental composition of $C_{15}H_{18}N_4O_6$ and chemical formula [1aR]-6-amino-8-[[aminocarbonyl)oxy]methyl]-1, 1a,2,8,8a,8b-hexahydro-8a-methoxy-5-methylazirinol[2',3':3,4]pyrrolo[1,2-a]indole-4,7-dione. It is sold under the trade name Mutamycin (Bristol-Myers Oncology Division, Bristol-Myers Squibb Company) as a sterile powder including mannitol.

By N-methyl mitomycin-C is meant an anti-bacterial anti-neoplastic substance, also called porfiromycin, isolated from a *Streptomyces ardus* fermentation broth and also isolated from *Streptomyces verticillatus*. N-methyl mitomycin-C has the elemental composition of $C_{16}H_{20}N_4O_5$ and chemical formula 6-amino-8-[[aminocarbonyl)oxy]methyl]-1,1a,2,8,8a,8b-hexahydro-8a-methoxy-1,5-dimethylazirinol[2',3':3,4]pyrrolo[1,2-a]indole-4, 7-dione.

By alkaloid is meant an amine containing compound originally isolated from a plant which may be commercially produced by extraction from plant material and purification, or by synthetic or semi-synthetic means.

By vincaalkaloid is meant alkaloid compounds originally isolated form the plant *Vinca rosea* Linn (*Catharanthus roseus* or Apocynaceae), and *Vinca minor*. These compounds are useful in several therapeutic categories including anti-neoplastics and vasodialators. Among these compounds are vinblastine, vincamine, vincine, vincaminine, vincinine, vincristine and the synthetic dimer of vinblastine, vindesine.

By vincristine is meant a vincaalkaloid identified as 22-Oxoyincaleukoblastine or leurocristine acid, originally isolated from the plant *Vinca rosea* Linn, having the elemental composition of $C_{46}H_{56}N_4O_{10}$, and molecular weight 824.94, and its sulfate salt having the elemental composition $C_{46}H_{56}N_4O_{14}S$ and molecular weight 923.04. The sulfate salt of vincristine is sold under the trade name Oncovin (Eli Lilly and Company) as a sterile liquid containing vincristine, mannitol, methylparaben, propylparaben and water with acetic acid and sodium acetate added for pH control.

By vinblastine is meant a vincaalkaloid identified as Vincaleukoblastine, originally isolated from the plant *Vinca rosea* Linn, having the elemental composition of $C_{46}H_{56}N_4O_9$, and molecular weight 811.00, and its sulfate salt having the elemental composition $C_{46}H_{60}N_4O_{13}S$ and molecular weight 909.10. The sulfate salt of vinblastine is sold under the trade name Velban (Eli Lilly and Company) as a sterile lyophilized plug containing no excipients.

By "anti-ulceration-effective amount" means an amount of a substance which when combined with a compound, cytotoxic drug, antibiotic or alkaloid, with or without an excipient and administered to a subject, significantly reduces the extent of ulceration that occurs, if any, compared to the extent of ulceration caused by the same amount of compound, cytotoxic drug, antibiotic or alkaloid, with or without an excipient when administered alone to a subject. Included in the phenomena defined herein as ulceration or ulcer are those phenomena usually associated with vesicants. See, Chapter 8 "Extravasation" in Cancer Chemotherapy, A Reference Guide, Linda Tenenbaum, W. B. Saunders Company, Harcourt Brace Jovanovich, Inc Philadelphia (1989); and Chapter 5 "Common Toxicities" in Cancer Chemotherapy Handbook, Robert T. Dorr and William L. Fritz, Elsevier, N.Y. The term ulceration or ulcer is not intended to include gastrointestinal, duodenal or intestinal irritation or ulceration associated with the oral administration of a number of oral analgesic and anti-inflammatory drugs such as indomethacin By vesicant is meant a chemotherapeutic agent which is topically toxic. If inadvertantly delivered outside of a vein, a vesicant has the potential to cause pain, cellular damage including cellulitis, tissue destruction (necrosis) with formation of a sore or ulcer and sloughing of tissues that may be extensive and require skin grafting. Examples of anti-cancer chemotherapeutic agents that are vesicants include but are not limited to Amsacrine, Dactinomycin, Daunorubicin, Doxorubicin, Idarubicin, Mechlorethamine, Mitomycin C, Vinblastine, Vincristine and Vindesine.

By anti-irritation-effective amount means an amount of a substance which when combined with a compound, cytotoxic drug, antibiotic or alkaloid, with or without an excipient and administered to a subject, significantly reduces the extent of irritation that occurs, if any, compared to the extent of irritation caused by the same amount of compound, cytotoxic drug, antibiotic or alkaloid, with or without an excipient when administered alone to a subject. Included in the phenomena defined herein as irritation are those phenomena usually associated with irritants. See, Chapter 8 "Extravasation" in Cancer Chemotherapy, A Reference Guide, Linda Tenenbaum, W. B. Saunders Company, Harcourt Brace Jovanovich, Inc Philadelphia (1989) and Chapter 5 "Common Toxicities" in Cancer Chemotherapy Handbook, Robert T. Dorr and William L. Fritz, Elsevier, N.Y. The term irritation is not intended to include gastrointestinal, duodenal or intestinal irritation or ulceration associated with the oral administration of a number of oral analgesic and anti-inflammatory drugs such as indomethacin.

By irritant is meant a chemotherapeutic agent that may produce pain and inflammation at the administration site or along the path of the vein (phlebitis) by which it is administered. Examples of anti-cancer chemotherapeutic agents which are irritants include but are not limited to Carmustine, Dacarbazine, Etoposide, Plicamycin, Etoposice, Streptozocin and Tenoposide.

By aqueous solution is meant solutions comprised of at least 90% water (weight/volume).

By cytotoxic is meant having the property of killing cells at low molar concentrations.

By antibiotic is meant compounds produced by microorganisms, and derivatives of such. compounds, which are capable at concentrations above a particular threshold concentration of killing other microorganisms and/or cells including mammalian cells.

By anti-cancer antibiotic is meant an antibiotic which is capable of killing cancerous cells.

By aminoglycoside antibiotic is meant an antibiotic compound containing nitrogen, usually in the form of at least one amino group wherein the compound also contains at least one glycoside bond to a sugar or saccharide moiety.

By daunorubicin is meant an antibiotic of the rhodomycin group, originally isolated from fermentation broths of *Streptomyces peuicetius* or *Streptomyces coentleonibidus* and its acid complexes particularly its hydrochloride complex. Daunorubicin is a glycoside formed by a tetracyclic aglycone daunomycinone and an amino sugar daunosamine. Daunorubicin has the elemental composition of $C_{27}H_{29}NO_{10}$ and chemical formula 8-Acetyl-10-[3-amino-2,3,6-tri-deoxy-α-L-lyxo-hexopyranosyl)oxy]-7,8,9,10-tetrahydro-6,8,-1 11-trihydroxy-1-methoxy-5,12-naphthacenedione, and molecular weight 527.51. Daunorubicin is sold under the trade name Cerubidine (Wyeth Ayerst Laboratories) as a sterile lyophilized powder with mannitol.

By doxorubicin is meant 14-hydroxydaunomycin a derivative of daunorubicin, and its acid complexes particularly its hydrochloride complex) having the elemental composition $C_{27}H_{29}NO_{11}$ and chemical formula 10-[(3-amino-2,3,6-tri-deoxy-α-L-lyxo-hexopyransoyl)oxy]-7,8,9,10-tetrahydro-6,8,-11-trihydroxy-8-(hydroxyacetyl)-1-methoxy-5,12-naphthacenedione and molecular weight 543.54. Doxorubicin HCL is sold as a generic drug by various manufacturers as a sterile lyophilized powder with mannitol and as a sterile solution of doxorubicin hydrochloride in sterile water for injection made iso-osmotic with sodium chloride and dextrose or other suitable added excipient.

By bleomycins is meant a group of related glycopeptide antibiotic substances including bleomycin-A, -B and -C and their components. Bleomycins are isolated from *Streptomyces verticillatus*. The bleomycins differ from one another in their terminal amines and show varying biological activity. Bleomycin $A_2$ is the main component of the bleomycin employed clinically as an anti-cancer antibiotic. Bleomycin-$A_2$ has the elemental composition of $C_{55}H_{84}N_{17}O_{21}S_3$ and chemical formula $N^1$-[3-(dimethylsulfonio)-propyl] bleomycinamide. Also included in this definition are the sulfate salts of the bleomycins.

By bleomycin is meant a mixture of basic cytotoxic glycopeptides produced by the growth of *Streptomyces verticillatus* or by other means and the sulfate salts thereof. In general HPLC analysis of bleomycin according to the definition shows the following contents, in order of elution as described in United States Pharmacopeia XXII: bleomycinic acid, bleomycin A2, bleomycin A5, bleomycin B2 and bleomycin B4. In a preferred embodiment of the invention Bleomycin as used herein conforms to the description of Bleomycin Sulfate in the United States Pharmacopeia XXII in that the content of the sulfate salts of bleomycin A2 is between 55% and 70%, bleomycin B2 is between 25% and 32% and bleomycin B4 is not more than 1%; and the combined percentage of the sulfate salts of bleomycins A2 and B2 is not less than 85%. A mixture of bleomycin A2 and bleomycin B2 (or their sulfate salts), wherein the concentration of bleomycin B2 is no less than 25% is also within the present definition of bleomycin. Bleomycin is sold under the trade name Blenoxane (Bristol-Myers Oncology Division, Bristol-Myers Squibb Company) as a sterile powder including mannitol.

By diazepam is meant is meant a benzodiazepine derivative having the chemical formula 7-chloro-1,3(dihydro-1-methyl-5-phenyl-2H-1,4-benzodiazepin-2-one and having a molecular weight of 284.7. Diazepam is sold under the tradename Valium (Roche Products, Inc.) and includes diazepam compounded with propylene glycol, ethyl alcohol, sodium benzoate and benzoic acid and benzyl alcohol.

Cytotoxic agents that are soluble in aqueous solution include but are not limited to antineoplastic compounds chosen from the following Table A. The solubilities of the compounds listed in Table A are compiled from a number of references including *The Merck Index* 10th Edition, the *Physicians Desk Reference* (1992 edition), and *The Cytotoxics Handbook* (Radcliff Medical Press, Oxford 1993) which are incorporated herein by reference.

TABLE A

Anti-cancer Agents Soluble in Aqueous Solution

| Name of Drug | Solubility | Reference |
| --- | --- | --- |
| dactinomycin | soluble in water-glycol | MI* |
| dacarbazine | soluble in 10% citric acid water | CTX** |
| daunorubicin | soluble in water | MI |
| doxorubicin | soluble in water | MI |
| vincristine sulphate | soluble in water (50% solution) | CTX |
| vinblastine sulphate | soluble in water (10% solution) | CTX |
| mithramycin | soluble in water | CTX |
| streptozocin | soluble in water | CTX |
| mitomycin C | soluble in water | MI |
| bleomycin | soluble in water | CTX |

*MI = Merck Index, 10th Edition
**CTX = The Cytotoxics Handbook (Radcliff 1993)

Bearing in mind the above described definitions, the present invention is for novel compositions of matter comprising an ulceration-reducing or irritation-reducing amount of a cyclodextrin compound and a cytotoxic compound. In a preferred embodiment the cyclodextrin is a substituted amorphous cyclodextrin, such as an alkyl or hydroxy alkyl substituted, including hydroxypropyl, hydroxyethyl, glucosyl, maltosyl and maltotrosyl derivatives of β-cyclodextrin or γ-cyclodextrin and the cytotoxic agent is one that is soluble in aqueous solution.

In general, the invention provides a composition of matter comprising an amorphous complex of cyclodextrin and any compound which can cause extravasation-associated ulceration or irritation when injected. While many such compounds are cytotoxic compounds, the compositions of matter according to the invention are not limited to cytotoxic compounds. For example certain sedative compounds when injected intravascualrly (iv) can cause severe ulceration if extravasation occurs. Such sedative compounds include but are not limited to diazepam compounds including diazepam.

Compositions of matter comprising an amorphous complex of cyclodextrin and a cytotoxic compound according to the invention may comprise a variety of different cytotoxic compounds used for a variety of therapeutic purposes. Such compositions according to the invention include an amorphous complex of cyclodextrin and an anti-cancer, antineoplastic, anti-fungal antibiotic, anti-bacterial antibiotic or chemical compound.

With respect to the compositions of matter comprising an amorphous complex of cyclodextrin and a cytotoxic compound which is a chemotherapeutic anticancer agent, the anticancer agent may be classified as a vesicant or an irritant. Examples of anti-cancer chemotherapeutic agents that are vesicants include but are not limited to Amsacrine, Dactinomycin, Daunorubicin, Doxorubicin, Idarubicin, Mechlorethamine, Mitomycin C, Vinblastine, Vincristine and Vindesine. Examples of anti-cancer chemotherapeutic agents which are irritants include but are not limited to Carmustine, Dacarbazine, Etoposide, Plicamycin, Etoposide, Streptozocin and Tenoposide. The effects of such agents on patients are found in the following Table B:

TABLE B

| Drug | Frequency of Phlebitis | Acute Local tissue Effects (infiltration) |
|---|---|---|
| Anthracyclines | | |
| Daunorubicin | Frequent | Tissue slough |
| Doxorubicin | Frequent | Large, spreading |
| Dactinomycin | Frequent | ulcerations; deep tissues |
| Idarubicin | Frequent | affected |
| Alkaloids | | |
| Vincristine | Infrequent | |
| Vinblastine | Frequent | Cellulitis if small dose |
| Tenoposide | Frequent | Slough if large dose |
| Nitrosoureas | | |
| Streptozotocin | Infrequent | Extravasation can cause |
| Carmustine | Infrequent | extreme pain and necrosis |
| Others | | |
| Mitomycin | Frequent | Pain and eventual tissue sloughing |
| Mithramycin | Infrequent | |
| Chromomycin A$_3$ | Frequent | Sever tissue sloughing |
| Decarbazine | Frequent | Pain, mild inflammation, slight necrosis |

In general, the composition of matter according to the invention will comprise a sufficient amount of the compound to exert its desired pharmacological effect when administered IV, whether it is for example sedation, anti-fungal activity, anti-neoplastic activity, and an amount of cyclodextrin compound sufficient to significantly reduce the extent of ulceration or irritation that would occur if a like amount of the compound were extravasated or administered IV without extravasation in the absence of the cyclodextrin compound. If the anticancer compound is a vesicant the composition of matter according to the invention will comprise a sufficient amount of the anticancer compound to exert its desired cytotoxic effect against targeted cancer cells and an anti-ulceration-effective amount of cyclodextrin, with or without an excipient. Likewise, if the anticancer compound is an irritant, the composition of matter according to the invention will comprise a sufficient amount of the anticancer compound to exert its desired cytotoxic effect against target cancer cells and anti-irritation-effective amount of cyclodextrin with or without an excipient.

The anti-cancer chemotherapeutic compounds that may comprise the composition according to the invention will be any anticancer chemotherapeutic compound that causes irritation, as defined herein, or ulceration, as defined herein, upon extravasation. The compound may be a synthetic chemical compound such a nitrogen mustard derivative for example mechlorethamine. The antineoplastic compound may be a plant alkaloid. With respect to such plant alkaloids, taxol, a chemical compound derived from the bark of the Pacific Yew tree, and pharmacologically active related compounds are contemplated. Also contemplated are water soluble compounds related to taxol such as taxotrere. While taxol is not water soluble, ulcerative activity caused by this anti-neoplastic compound may be significantly reduced by administration with hydroxypropyl-β-cyclodextrin and it is believed that further improvement in anti-ulcerativie effect will be obtained with amorphous γ-cyclodextrins Also contemplated in the compositions according to the invention are the vinca alkaloids. Such vinca alkaloids as vincristine and vinblastine and vindisine are particularly strong vesicants.

Also among the anti-cancer chemotherapeutic compounds that may comprise the composition according to the invention are alkylating agents which are used as anti-cancer chemotherapeutics such as dacarbazine and streptozocin.

The composition according to the invention may comprise a complex of cyclodextrin and a microbial produced antibiotic compound which is subsequently purified or partially purified. Cytotoxic antibiotics that may be part of the composition according to the invention include those administered as anti-cancer agents, such as the mitomycin including but not limited to mitomycin-c, the bleomycins including but not limited to mixtures predominating in bleomycin A2 and B, daunorubicin, doxorubicin, plicamycin and dactinomycin. All of the forgoing are soluble in aqueous solution.

Anti-cancer agents which are protein biological response modifier such as interleukin-2 or Tumor Necrosis Factor are not intended as the anti-cancer agents of the compositions according to the invention since they do not cause ulceration or irritation as defined herein resulting from extravasation; however compositions of matter which include such protein biological response modifiers and an anti-neoplastic chemotherapeutic agent which does cause extravasation associated irritation or ulceration are intended as compositions according to the invention.

The composition according to the invention may comprise a complex of cyclodextrin and other cytotoxic anti-fungal antibiotic agents such as amphoteracin B.

Additionally, the compositions according to the invention include pharmaceutical compounds which are not administered to achieve a specific cytotoxic effect, but which may also result in extravasation-associated ulceration. Such compounds which may be part of the compositions including cyclodextrin according to the invention include, for example certain sedative compounds typified by benzodiazapine compounds including but not limited to diazepam. In this instance, the composition according to the invention comprises an amount of the compound sufficient to exert the desired pharmacological effect when administered iv and an anti-ulceration or anti-irritation effective amount of the cyclodextrin compound.

The compositions of matter according to the invention may also include, in addition to the complex of cyclodextrin and a chemotherapeutic compound, carriers, bulking agents and other pharmaceutically acceptable excipients such as mannitol, sorbitol, lactose, sucrose and the like. Surprisingly, it has been found that chemotherapeutic compounds and such excipients, particularly mannitol, when formulated with cyclodextrin do not cause any significant ulceration if extravasated when administered to mammalian subjects.

The cyclodextrin of the compositions according to the invention may be α-, β-, or γ-cyclodexrin. α-cyclodextrin contains six glucopyranose units; β-cyclodextrin contains seven glucopyranose units; and γ-cyclodextrin contains eight glucopyranose units. The molecule is believed to form a truncated cone having a core opening of 4.7–5.3 Å, 6.0–6.5 Å and 7.5–8.3 Å in α-, β-, or γ-cyclodextrin respectively. The composition according to the invention may comprise a mixture of two or more of the α-, β-, or γ-cyclodextrins. Usually, however the composition according to the invention will comprise only one of the α-, β-, or γ-cyclodextrins. The particular α-, β-, or γ-cyclodextrin to be used with the particular cytotoxic compound to form the compositions according to the invention may be selected based on the known size of the molecule of the cytotoxic compound and the relative size of the cavity of the cyclodextrin compound. Generally if the molecule of the cytotoxic compound is relatively large, a cyclodextrin having a larger cavity is used to make the composition according to the invention. Furthermore, if the cytotoxic compound is administered with an excipient it may be desirable to use a cyclodextrin compound having a larger cavity in the composition according to the invention.

The unmodified α-, β-, or γ-cyclodextrins are less preferred in the compositions according to the invention because the unmodified forms tend to crystalize and are relatively less soluble in aqueous solutions. More preferred for the compositions according to the invention are the α-, β-, and γ-cyclodextrins that are chemically modified or substituted. Chemical substitution at the 2,3 and 6 hydroxyl groups of the glucopyranose units of the cyclodextrin rings yields increases in solubility of the cyclodextrin compound.

Most preferred cyclodextrins in the compositions according to the invention are amorphous cyclodextrin compounds. By amorphous cyclodextrin is meant non-crystalline mixtures of cyclodextrins wherein the mixture is prepared from α-, β-, or γ-cyclodextrin. In general, the amorphous cyclodextrin is prepared by non-selective alkylation of the desired cyclodextrin species. Suitable alkylation agents for this purpose include but are not limited to propylene oxide, glycidol, iodoactamide, chloroacetate, and 2-diethylaminoethlychloride. Reactions are carried out to yield mixtures containing a plurality of components thereby preventing crystallization of the cyclodextrin. various alkylated cyclodextrins can be made and of course will vary, depending upon the starting species of cyclodextrin and the alkylating agent used. Among the amorphous cyclodextrins suitable for compositions according to the invention are hydroxypropyl, hydroxyethyl, glucosyl, maltosyl and maltotrosyl derivatives of β-cyclodextrin, carboxyamidomethyl-β-cyclodextrin, carboxymethyl-β-cyclodextrin, hydroxypropyl-β-cyclodextrin and diethylamino-β-cyclodextrin. In the compositions according to the invention hydroxypropyl-β-cyclodextrin is preferred although the α- or γ-analogs may also be suitable. The particular alkylated α-, β-, or γ-cyclodextrin to be used with the particular cytotoxic compound to form the compositions according to the invention will be selected based on the size of the molecule of the cytotoxic compound and the relative size of the cavity of the cyclodextrin compound. As with the unsubstituted cyclodextrins mentioned above, it may be advantageous to use alkylated cyclodextrin having a larger cavity when the composition according to the invention also includes an excipient. The use of a particular α-, β-, or γ-cyclodextrin with a particular cytotoxic compound or cytotoxic compound and excipient in the compositions according to the invention may of course be optimized based on the effectiveness in reducing ulceration or irritation.

Another significant factor in determining the anti-ulcerative and anti irritation effects of complexes of substituted cyclodextrins and cytotoxic drugs is the degree of substitution of substituent groups in the cyclodextrin molecule, whether it is α-, β-, or γ-cyclodextrin. By degree of substitution is meant the number of substituent molecules per molecule of cyclodextrin. In the composition according to the invention a higher average degree of substitution of substituent groups in the cyclodextrin molecule is believed to be preferable. Such substituent groups are exemplified by those mentioned in the paragraph above. A degree of substitution in the range of about 4 to about 10 for hydroxypropyl substituents may be effective with mitomycin-c and doxorubicin. A degree of substitution in the range of about 5 to about 9 is preferred and is expected to be anti-ulceration effective for compositions including both water soluble anti-neoplastic agents such as those mentioned herein above and water insoluble antineoplastic agents such as taxol.

As mentioned above, the compositions of matter of the invention comprise a cytotoxic compound and cyclodextrin. The relative amounts of cytotoxic compound and cyclodextrin will vary depending upon the relative toxicity of the compound and the effect of the cyclodextrin on the compound. In general, the ratio of the weight of cytotoxic compound to the weight of cyclodextrin compound will be in a range between 1:20 and 1:5000. Within this range, the ulcerative effects of many cytotoxic compounds will be significantly reduced when the ratio of the weight of cytotoxic compound to the weight of cyclodextrin compound is in a range between 1:50 and 1:2000. A weight to weight ratio in a range of 1:50 to 1:2000 and more preferably in a range of 1:50 to 1:800 cf cytotoxic chemotherapeutic compound to cyclodextrin are believed to be effective for a number of vesicant anti-cancer chemotherapeutics. For example Mitomycin in a ratio of between 1:100 to 1:300 (drug to cyclodextrin) significantly reduces the extent of ulceration clue to intradermally deposited mitomycin C. When mitomycin C in a weigh to weight ratio with β-hydroxypropyl cyclodextrin of 1:160 was injected intradermally in a mammalian subject the lesion resulting from the injection was about one third the size of the lesion cause by intradermal injection of the same amount of mitomycin C without the cyclodextrin compound. Furthermore when mitomycin-C together with the excipient mannitol in a weight to weight ratio with β-hydroxypropyl cyclodextrin of 1:400 (mitomycin: β-hydroxypropyl cyclodextrin) was injected intradermally in a mammalian subject, the lesion resulting from the injection was eliminated entirely in 80% of the test subjects, and in the remaining test subjects the lesion was about one tenth the size of the lesion cause by intradermal injection of the same amount of mitomycin C and mannitol without the cyclodextrin compound.

The compositions of matter according to the invention may by supplied as a powder comprising the active pharmaceutical compound and cyclodextrin compound. If the composition is to be administered parenterally, for example iv, the composition of matter will be rendered sterile prior to such administration. Any of the several known means for rendering such pharmaceutical preparations sterile may be used so long as the active pharmaceutical compound is not inactivated. If the active pharmaceutical compound is heat stable, the composition of matter according to the invention may be heat sterilized. If the cytotoxic compound is not heat stable but is not photodegraded the composition may be sterilized by exposure to ultraviolet light. Alternatively, the composition of matter if in a powder form may be gas sterilized using for example ethylene oxide gas. In another alternative, the composition of matter according to the invention may be filter sterilized using a 2 micron filter. If the composition of matter is a aqueous liquid, it may be filled in a sterile container and supplied as a sterile liquid ready for further dilution or injection neat Alternatively such sterile liquids may be freeze dried or lyophilized in a sterile container and capped.

In general the compositions of matter according to the invention will be made by dissolving the cyclodextrin in water and adding the active compound to the aqueous cyclodextrin solution. Excipients, if any are desired may be added with or subsequent to adding the active compound. The resulting solution may be sterilized using any of the known methods appropriate to preserving the active compound. Alternatively, the components may be sterilized by any of the known methods appropriate to preserving the active compound prior to mixing in water an may be mixed using sterile equipment and technique. The solution may be lyophilized in sterile containers and capped. Prior to use the lyophilized composition of matter may be reconstituted using sterile water for injection.

It will be understood that the compositions of matter according to the invention provide novel methods of controlling and reducing the incidence of ulceration associated with extravasation and irritation associated with intravenous administration of many pharmaceutical compounds. The compositions of matter according to the invention provide a method for reducing the likelihood of ulceration in subjects in need of parenteral treatment with compounds that if extravasated have the potential for causing ulceration, by administering to such subjects a preparation comprising at least one compound that if extravasated has the potential for causing ulceration and an anti-ulceration-effective amount of cyclodextrin or amorphous cyclodextrin. Furthermore, the compositions according to the invention provide a method for reducing the likelihood of irritation in subjects in need of parenteral treatment with compounds that when administered parenterally, particularly intravenously, have the potential for causing irritation, by administering to such subject a preparation comprising at least one compound that has the potential for causing irritation and an anti-irritation-effective amount of cyclodextrin or amorphous cyclodextrin.

It will be understood that the present invention provides both compositions of matter and methods for the substantial reduction in injuries caused as a result of extravasation. While it is heretofore known that compositions of amorphous cyclodextrin and compounds that are not soluble in water because they are lipophilic have the property of reducing precipitation of compounds at or near the injection site, the heretofore known compositions and methods fail to make any observation on the effect of extravasated compounds, or the amounts of amorphous cyclodextrin needed to prevent the ulcerative effects of such extravasated compounds.

Accordingly, the present invention is directed to compositions comprising anti ulceration-effective amounts of amorphous cyclodextrin and compounds that otherwise cause ulceration when extravasated. Such compounds may be soluble in aqueous solution or alternatively may be lipophilic and as a result tend to precipitate in aqueous solutions. Since amorphous cyclodextrins are taught in the art to solubilize compounds that are not soluble in water, it is surprising, and heretofore unobserved and unreported that compositions of matter comprising amorphous cyclodextrin and such insoluble compounds, which have been rendered soluble by complexation with cyclodextrin do not lead to ulceration when extravasated. This observation is especially surprising because water soluble cytotoxic compounds frequently cause ulceration when extravasated, and it would be expected that lipophilic cytotoxic compounds rendered soluble by complexation with cyclodextrin would similarly remain cytotoxic.

Even more unexpected is the effect of forming complexes with cyclodextrin compounds on ulceration associated with extravasation using cytotoxic compounds that are soluble in aqueous solution and which are not expected to precipitate at or near the site of injection. Indeed, the literature on extravasation toxicity indicates that the problem of toxicity associated with extravasation of water soluble compounds is exacerbated by the solubility of these compounds. Such water soluble toxic compounds rather than precipitating appear to spread throughout the limb when extravasated. It is thus unexpected that the ulcerative toxicity of such compounds would be curtailed by complexation with a cyclodextrin compound or that complexation of such compounds that are soluble in aqueous solution with a cyclodextrin compound would occur at all.

The invention will be better understood from the following examples which are intended to be merely illustrative of the invention and are not intended to be limiting.

EXAMPLE I

Effects of Hydroxypropylcyclodextrin (HPCD) on Mitomycin-c Solubility

Purified mitomycin C was divided into aliquot ranging from 0 to 10 mg and were place in pre-weighed 12×75 mm glass tubes. To each tube was added 1 ml of double distilled water, 20% HPCD (weight/volume (w/v) in double distilled water) or 40% HPCD w/v. HPCD had a degree of substitution of 7. Each tube was vortexed for 1 minute and allowed to stand at room temperature for 1 hour at which time they were revortexed for 1 minute. Tubes were then centrifuged for 4 minutes in a Triac centrifuge to concentrate the undissolved mitomycin-c in the bottom of the tube. The dissolved mitomycin, along with the diluent was decanted. The tubes containing the undissolved mitomycin-c were dried at 80° C. and reweighed to determine the weight of insoluble mitomycin-c. The results are shown in Table I.

TABLE I

| % HPβCD | dose mitomycin-c (mg) | mg insoluble | % solubility |
|---|---|---|---|
| ($H_2O$) | 0 | 0 | — |
|  | 1 | 0 | 100 |
|  | 2.5 | 0 | 100 |
|  | 5 | 2.7 | 46 |
|  | 10 | 6.0 | 40 |
| 20% | 0 | 0 |  |
|  | 1 | 0 | 100 |

TABLE I-continued

| % HPβCD | dose mitomycin-c (mg) | mg insoluble | % solubility |
|---------|----------------------|--------------|--------------|
|         | 2.5                  | 0            | 100          |
|         | 5                    | 0            | 100          |
|         | 10                   | 4.7          | 53           |
| 40%     | 0                    | 0            |              |
|         | 1                    | 0            | 100          |
|         | 2.5                  | 0            | 100          |
|         | 5                    | 0            | 100          |
|         | 10                   | 1.1          | 89           |

In water, mitomycin-c was completely soluble up to a concentration of 2.5 mg/ml, but solubility was limited to 46% and 40% at the 5 and 10 mg/ml concentrations, respectively. Hence in water the limits of solubility of mitomycin-c appeared to be about 2.5 mg/ml. Solubility of mitomycin-c was improved in HPCD. In 20% HPCD mitomycin-c was completely soluble at 5 mg/ml and 50% soluble at 10 mg/ml, indicating that the solubility limits in 20% HPCD was about 5 mg/ml. In 40% HPC, mitomycin-C was completely soluble through 5 mg/ml. These data indicate that 40% HPCD increased mitomycin-c solubility by 3- to 4-fold.

EXAMPLE II

Effects of HPCD on Mitomycin-c Extravasation Toxicity

Based upon the solubility study of Example I and a preliminary animal evaluation to optimize lesion size, 1.25 mg mitomycin-c in 0.5 ml of solvent (water or 40% HPCD) was used. Eighteen rats were divided into 3 groups. These groups of 6 rats each received the following injections at separate sites on the back:

| | |
|---|---|
| Group 1: | Saline (0.5 ml) then saline (0.5 ml) |
| | Saline (0.5 ml) then 40% HPCD (0.5 ml) |
| | 40% HPCD (0.5 ml) |
| Group 2: | Mitomycin-c in saline (0.5 ml) |
| | Mitomycin-c in 40% HPCD (0.5 ml) |
| Group 3: | Mitomycin-c in saline (0.5 ml) then saline (0.5 ml) |
| | Mitomycin-c in saline (0.5 ml) then 40% HPCD (0.5 ml) |

Group 1 rats represent three different control injections.; Group 2 rats test mitomycin-c diluted in saline versus mitomycin-c in 40% HPCD; and Group 3 rats test the effects of subsequent saline or HPCD injection on mitomycin-c toxicity. HPCD had a degree of substitution of 7. All injections were made into the skin and the accuracy of the intradermal injection was verified by local blanching of the skin at the time of the injection. For Group 1 and 2, when sequential injections were made, the injection needle was left in place following the first injection and the second injection immediately followed the first. This insured that the second injection was delivered to the same intradermal site as the first. The results are shown in Table II.

TABLE II

Effects of Cyclodextrin on Mitomycin-c Extravasation Toxicity-Lesion Diameter (cm)

|  | Day 1 | Day 2 | Day 3 |
|---|---|---|---|
| Saline-Saline | 0 ± 0 (6) | 0 ± 0 (6) | 0 ± 0 (6) |
| Saline + 40% HPCD | 0 ± 0 (6) | 0.35 ± 0.09 (6) | 0.26 ± 0.097 (6) |
| 40% HPCD | 0 ± 0 (6) | 0.57 ± 0.14 (6) | 0.6 ± 0.14 (6) |
| mit-c + saline | 0.95 ± 0.19 (6) | 1.3 ± 0.12 (6) | 1.45 ± 0.15 (4)[+] |
| mit-c + 40% HPCD | 0.36 ± 0.21 (6)* | 0.53 ± 0.16 (6) | 0.58 ± 0.19 (4)[+] |
| mit-c then Saline | 1.13 ± 0.05 (6) | 1.5 ± 0.15 (6) | 1.52 ± 0.25 (3)[+] |
| mit-C then HPCD | 1.28 ± 0.09 (6) | 1.31 ± 0.27 (6) | 0.4 ± 0.25 (3)[+] |

[+]n is reduced because of deaths; *p <0.05 vs the mitomycin-c saline group; depicted are mean ± SEM (n = number of samples.)

Saline injection had no adverse effects when given intradermally. HPCD injections cause a small lesion whether it was administered after a saline injection (sal ne+40% HPCD=20% HPCD at the injection site) or alone 40% HPCD in 0.5 ml.) The lesion produced by HPCD appeared to be concentration dependent and peaked at 4 days post injection. As the 20% HPCD lesion was small (3.5 mm) this dose of HPCD would appear to be optimal for the injections. However as all injections were done on the same day and in as much as 0.40% HPCD was chosen, the following data should be viewed with respect to the contribution of HPCD to the lesion size. Mitomycin-c diluted in saline caused a 0.95 cm lesion by day I which increased in size to 1.45 cm by day 6 post injection. By contrast when mitomycin-c was diluted in 40% HPCD, lesion size was reduced by ⅔ each at each sampling time. The mitomycin-c-HPCD lesion was significantly smaller and it appears that mitomycin -C in HPCD can prevent greater than 50% the measurable extent of ulceration associated with extravasation of the chemotherapeutic agent.

Administration of mitomycin-c followed by HPCD appeared to have little beneficial effect on the size of lesions. This may be because (i) mitomycin-c rapidly interacts with tissue in a manner which cannot be reversed by HPCD or (II) complexation of mitomycin-c and HPCD does not occur effectively in vivo. This latter possibility is indicated by the observation that during the intradermal injection, mitomycin-c (a blue color) was pushed to the periphery of the injection site by the subsequent HPCD injection. The high viscosity of the HPCD displaced the drug, rather than mixed with the mitomycin-c at the injection site. The subsequent injection of 40% HPCD was ineffective in preventing extravasation toxicity. As a result it is clear that preparation of mitomycin-c in HPCD is superior to attempts to mitigate ulceration caused by extravasated mitomycin-C.

EXAMPLE III

Effects of HPCD on Mitomycin with Mannitol as Excipient-Extravasation Toxicity

Vials of mitomycin containing 10 mg of mannitol per mg mitomycin-c (Bristol Myers Oncology Division of Bristol Myers Squibb Company [herein after referred to as MM, 1 Unit (U) MM=1 mg mitomycin C and 10 mg mannitol]) were diluted to 1 mg mitomycin-c/ml $H_2O$ or 40% HPCD. HPCD had a degree of substitution of 7. Vials were vortexed for 1 min, allowed to sit at room temperature for 1 hr and were vortexed again for 1 min. Five rats received an injection of 1 U MM/ml saline as described above on one side and 1 UMM/ml 40% HPCD on the opposite side of the back. The results are reported in Table III.

TABLE III

Effects on Ulceration associated with Extravasation of HPCD - Mitomycin with Mannitol as Measured by Lesion Diameter (cm)

|  | Day 1 | Day 4 |
|---|---|---|
| Mitomycin-c/mannitol in H$_2$O | 0.865 ± 0.05 (5) | 0.93 ± 0.064 (5) |
| Mitomycin-c/mannitol in 40% HPCD | 0.04 ± 0.035 (5)+ | 0.13 ± 0.12 (5)+ |

+ 4 of 5 rats showed no lesion and were assigned a lesion diameter of 0; * p <0.05 vs the mitomycin-c with mannitol-H$_2$O group. Depicted are mean ± SEM (n = number of samples)

MM in H$_2$O caused lesions in all 5 of the rats tested. MM caused lesions in all 5 of the rats tested. The average lesion size was 0.865 cm on day 1 post administration and increased to 0.93 cm on day 4 post administration. By contrast, MM complexed with 40% HPCD caused no a lesion in 4 of 5 rats tested. The one observed lesion measured 0.04 cm on day 1 and 0.013 cm on day 4 post administration.

EXAMPLE IV

Preservation of Mytomycin-C Toxicity

The observations concerning toxicity as shown by change in body weight is in Study 2 and 3 is shown in Table IV.

TABLE IV

Effects of Intradermal Administration of Mitomycin-c on Body Weight in Male Rats

| Study 2 | Day 0 | Day 1 | Day 4 | Day 6 |
|---|---|---|---|---|
| Group 1 (vehicles) | 326 ± 5 | 335 ± 5 | 341 ± 9 | 345 ± 6 |
| Group 2 mitomycin-c (2.5 mg total dose) | 337 ± 6 | 351 ± 7 | 298 ± 5* | 250 ± 2* |
| Group 3 mitomycin-c (2.5 mg total dose) | 343 ± 7 | 354 ± 9 | 286 ± 12* | 261 ± 11* |

| Study 3 | Day 0 | Day 1 | Day 4 |
|---|---|---|---|
| Group 1 MM (mitomycin-c-mannitol) 2.0 mg mitomycin-c dose | 191 ± 7 | 185 ± 8 | 144 ± 5* |

*p <0.05 vs day 0 body weights; depicted are mean ± SEM.

These studies were terminated at 4 to 6 days post administration respectively as the dose of mitomycin needed to produce consistent and readily measurable lesions was very toxic to the rats. In Study 2 and 3, Mitomycin-c treated rats lost about 25% of their initial body weight over 6 and 4 days post administration respectively. All animals receiving MM had sever diarrhea, were cold to the touch and were inactive Five of 12 mitomycin-treated study 2 rats died between days 4 and 6. All study 3 rats died by day 6. The small initial size of the study 3 rats may have contributed to the increased mortality. In no case did the systemic toxicity influence the formation skin lesion which were apparent by day 1 prior to occurrence of any diarrhea or decrease in weight gain.

Systemic toxicity of the HPCD-mitomycin and HPCD-MM formulations was not reduced as compared to equivalent doses of mitomycin-C in water indicating that the toxicity required for effectiveness of mitomycin-c for use as an anticancer agent is not impaired by formation of the mitomycin-c-cyclodextrin complex or the mitomycin-c-cyclodextrin complex with excipient.

EXAMPLE V

Doxorubicin HPCD Formulation

Animals were injected with one of 5 solutions prepared as follows: Solution A consisted of 2.5 mg mannitol and 0.2 gm HPCD in 0.5 ml of saline. The mannitol dose is equal to that used in the doxorubacin commercial vehicle and the HPCD was 20% weight/volume (of saline). Solution B consisted of 2 mg doxorubacin and 2.5 mg mannitol/0.5 ml saline (hereafter referred to as doxorubacin in commercial vehicle). Solution C consisted of 2 mg doxorubacin, 2.5 mg mannitol and 0.2 gm HPCD in 0.5 ml saline hereafter referred to as doxorubacin in 20% HPCD). All HPCD had a degree of substitution of 7.

Animal Use

Male Charles Rivers CD (Sprague-Dawley) rats were anesthetized with metaphane (inhalant), marked for continuous identification and weighed. The hair on the mid-section of their back was shaved, the skin was thoroughly scrubbed with 70% ethanol and one of the aforementioned 5 solutions was administered by a single intradermal injection using a sterile 1 cc tuberculin syringe and a 27 gauge needle. Eight rats were treated per group.

At 1, 3, 6, 13 and 20 days after the injection, rats were weighed, the size of the lesion was measured, the lesion was described and the general health of the rats was assessed and recorded. Lesion diameter was determined by measuring the greatest and least extent of the lesion and the average of the 2 measurements was reported. The measurement of lesions and inspection of animals was done without anesthesia.

Results

Body Weight

The effects of intradermal injection of 20% HPCD and doxorubacin on body weight in adult male rats is depicted in Table 1. As we had previously reported, 20% HPCD has no effect on body weight as animals continued to gain weight throughout the sampling period. This is the expected weight response of young adult male rats. Treatment with doxorubacin in commercial vehicle (CV) had no adverse effect on body weight and treatment with doxorubacin in 20% HPCD only modestly reduced the rate of weight gain in rats. Indeed, this latter group of rats appeared to gain weight normally through the 1st post-inject on week, then showed a slight decline in the rate of weight gain thereafter. All animals treated intradermally with doxorubacin appeared to be healthy and showed no adverse effects of the drug, other than the skin lesions, as intended.

Lesion Size

The effects of intradermal administration of doxorubacin on lesion size is depicted in Table 3. Intradermal injection of 0.5 ml of 20% HPCD caused no effect in 7 of 8 rats tested. The remaining one animal developed a small lesion (0.3 cm diameter) which was observed on day 3 and 6 and which had healed completely by day 13 post injection. This observation is consistant with previous observations. Doxorubacin in CV caused necrotic lesions of the skin in all 8 rats tested which persisted throughout the observation period. The lesions were evident by day 3, peaked in diameter at 0.73±0.04 cm on day 6 and were slightly reduced in size on day 13 and 20.

Doxorubicin in 20% HPCD showed a different response. On day 3 only 4 of 8 rats had shown lesions, on days 6 and 13, 6 of 8 rats exhibited lesions and on day 20, 4 of 8 rats had lesions. In the Doxorubacin in 20% HPCD group, 4 of the rats showed lesions that persisted through day 20. Two rats failed to exhibit lesions at any sampling time. The final two rats, showed small lesions which first appeared by day 6, were present at day 13 and were completely healed by day 20. As a result, the diameter of the lesions produced were lower in the Doxorubicin-20% HPCD group than in the Doxorubicin-in CV group at each sampling time from day 3 to day 20.

Description of Lesions

For 7 of 8 rats injected with the vehicle, no lesion formed and there was no evidence of an injection effect by the 1st day after injection. In the single animal which showed a lesion, a small, brown (necrotic) area was evident by day 3, but had healed by day 13.

For animals injected with doxorubacin in c.v., rats exhibited at the time of the injection and at 1 day post-injection, a red colored area of the skin indicative of the deposition of the red colored doxorubacin. On the 1st post-injection day, the center of this reddened area was brown (necrotic) in 4 of 8 rats, but it was too small to measure. By day 3 post-injection, lesions had formed in all 8 rats and scabs had covered the damaged tissue. These scabs were well defined, persisted through the remainder of the study and were used to measure the extent of the lesions.

Animals injected intradermally with doxorubacin formulated in 20% HPCD showed 2 subgroups. The first subgroup of 4 rats showed lesions which were similar in their progression and size to those seen in the doxorubacin-c.v. group. That is, these animals showed red coloration at the injection site on day one and exhibited lesions with scabs by day 3 postinjection. By contrast, the second subgroup, which consisted of 2 animals which did not develop lesion and 2 animals which developed small, rapidly healing lesions, showed a different response to injection. First at one day after injection, the red coloration (drug) at the injection site was either non-existent or very faint. Thereafter, 2 animals failed to develop skin lesions, and 2 animals exhibited lesions which were small in size and rapidly healed. An example of this latter, small lesion subgroup is animal #13, which on day 4 of the day of the photograph, a red area was noted, but no lesion was present. This rat would develop a small lesion which was present on day 6 smaller on day 13 and completely healed by day 20.

Brief Interpretation of Data

From the data presented here and from my previous report, it appears that HPCD may be effective in reducing skin lesion size and the incidence of skin lesions by dispersing the complexed drug from the injection site. In our previous study, we noted that lesions which form following intradermal injection were more diffuse in nature when mitomycin was formulated in HPCD versus commercial vehicle. In the present study, we found two evidences for the same phenomena. First, at one day following doxorubacin-HPCD injections, one-half of the injected-rats failed to exhibit or showed only faint evidence of the red color associated with drug deposition. These animals were either lesion free or subsequently formed only small lesions.

TABLE V

| Treatment* | Days Post Injection | | | | |
|---|---|---|---|---|---|
| | 0 | 3 | 6 | 13 | 20 |
| HPCD/ vehicle | 0 | 0.03 ± 0.03 | 0.03 ± 0.04 | 0 | 0 |
| Doxorubicin/ vehicle | 0 | 0.63 ± 0.04 | 0.73 ± 0.04 | 0.66 ± 0.03 | 0.53 ± 0.04 |
| Doxorubicin/ 20% HPCD | 0 | 0.375 ± 0.14 | 0.59 ± 0.14 | 0.44 ± 0.12 | 0.3 ± 0.12 | p < 0.05 vs Doxorubicin in vehicle group

EXAMPLE VI

Taxol Formulations of HPCD

Solutions for Injection

Animals were injected with one of the following solutions. Solution A consisted of 20% (w/v) of HPCD and represented the vehicle for injection. Solution B consisted of a 50% ethanol solution of Taxol (1.25 mg/0.5 ml; hereafter referred to as Taxol in CV). Solution C consisted of 20% HPCD in ethanol/water (1/1, w/v; hereafter referred to as Taxol in HPCD). HPCD had a degree of substitution of 7.

Male Charles Rivers CD rat eight rats per group were prepared and injected as in Example V with a single intradermal injection of the indicated solution using a sterile 1 cc tuberculin syringe and a 27 g needle. At 1, 3, and 7 days after the injection, rats were weighed, the size of the lesion was determined, the lesions were described and the general health of the rats was assessed and recorded.

Body Weight and General Health

The effects of Taxol administration on body weight is depicted in Table VI. All animals showed an increase in body weight following the injection. The range of increase did not differ significantly between groups. These data indicate that the drugs were well tolerated by the animals regardless of the vehicle used for the injection. Additionally, the animals appeared to be in good health and no abnormalities, other than the induced lesions, were observed.

Lesion Size

The effects of Taxol injection intradermally on lesiforming lesions of the skin are shown in Table 2. The 20% HPCD vehicle itself, caused no lesions. Taxol in CV caused lesions of 1.52±0.4 cm diameter by day 1, in all 8 rats injected, and the size of the lesions remained the same through the remaining sampling periods. When formulated in HPCD, Taxol caused no lesions by day 1, and on days 3 and 7, six of 8 injected rats showed lesions. The lesion size was reduced to ⅓ of that observed in Taxol-CV injected rats on both day 3 and 7.

Description of Lesions

The lesions produced by Taxol in CV were necrotic lesions which destroyed the skin at the injection site a manner which clearly related to the deposition of drug at the injection site. On day one, the lesions were characterized by a large white center with a red halo around it. The lesions were very consistent in diameter as reflected in the small standard error in the data for the Taxol-HPCD group (see Table). By day three, lesions were maximal in size, were fully necrotic and had scabbed. Little change occurred through day 7. When formulated in HPCD, Taxol failed to cause lesions on day 1; at this time, 5 of 8 rats showed evidence of redness at the site of deposition of the drug. On day 3, the lesions observed were similar to these seen in the Taxol-CV group, but were smaller in size by ⅔. On day 7 all lesions were well healed and again at this time were smaller in size than those seen in the Taxol-CV group.

The results of these studies indicate that HPCD exerts a protective effect on skin when Taxol is deposited into an intradermal site. Indeed, this effect is substantial, resulting in a ⅔ reduction in lesion size.

TABLE VI

| Treatment | Day 1 | Day 3 | Day 7 |
|---|---|---|---|
| Vehicle | 0 | 0 | 0 |
| Taxol CV | 1.52 ± 0.04 | 1.58 ± 0.05 | 1.54 ± 0.04 |
| Taxol HPCD | 0 | 0.52 ± 0.12 | 0.52 ± 0.12 | p > = 0.05 vs CV control

The compositions of matter according to the invention offer several advantages over the existing formulations of active compounds administered parenterally, especially intravenously. By reducing toxicities associated with the use of these active compounds, it may be possible to reduce the volume of the formulation in solution that is administered to the patient without altering the effective dose of the active compound. Thus within the spirit of the invention are improved formulations and methods of using the same when administering such formulations to patients. As mentioned herein above a number of excipients may be appropriate for use in the formulations which comprise the composition according to the invention. The inclusion of excipients and the optimization of their concentration for their expected characteristics such as for example ease of handling or as carrier agents will be understood by those ordinarily skilled in the art not to depart from the spirit of the invention as described herein and claimed hereinbelow.

I claim:

1. A composition of matter comprising an anti-ulceration effective amount of a substituted cyclodextrin compound and a nitrogen mustard compound.

2. The composition of claim 1, further comprising an excipient.

3. The composition of claim 2, wherein said excipient is a sugar alcohol.

4. The composition of claim 1, wherein the weight ratio of the nitrogen mustard compound to the cyclodextrin compound ranges from 1:20 to 1:5000.

5. The composition of claim 1, wherein the weight ratio of the nitrogen mustard compound to the cyclodextrin compound ranges from 1:50 to 1:800.

6. The composition of claim 1, wherein the nitrogen mustard compound is mechlorethamine.

7. The composition of claim 1 wherein the substituted cyclodextrin compound is amorphous.

8. The composition of claim 1, wherein the substituted cyclodextrin compound is an α-cyclodextrin, β-cyclodextrin, or γ-cyclodextrin.

9. The composition of claim 1, wherein the substituted cyclodextrin compound is a hydroxypropyl, hydroxyethyl, glucosyl, maltosyl maltrosyl derivative of β-cyclodextrin, carboxyamidomethyl-β-cyclodextrin, carboxymethyl-β-cyclodextrin, or diethylamino-β-cyclodextrin.

10. The composition of claim 1, wherein the degree of substitution of the substituted cyclodextrin compound is about 5 to about 9.

11. The composition of claim 3, wherein the sugar alcohol is mannitol.

12. The composition of claim 3, wherein the sugar alcohol is sorbitol.

13. The composition of claim 3, wherein the sugar alcohol is sucrose.

14. A method for reducing ulceration or irritation in a host arising through parenteral treatment of the host with a nitrogen mustard compound that has the potential for causing irritation or ulceration when extravasated, comprising:

administering to the host a preparation comprising an aqueous solution of the nitrogen mustard compound and an anti-ulceration effective or anti-irritation effective amount of a substituted cyclodextrin compound.

* * * * *